(12) United States Patent
Richter et al.

(10) Patent No.: US 11,674,015 B2
(45) Date of Patent: Jun. 13, 2023

(54) POLYAMIDES WITH IMPROVED OPTICAL PROPERTIES

(71) Applicant: BASF SE, Ludwigshafen (DE)

(72) Inventors: Florian Richter, Mannheim (DE); Rainer Xalter, Heidelberg (DE); Hye Jin Park, Osnabrueck (DE); Raphaël Dabbous, Riehen (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/565,273

(22) PCT Filed: Apr. 13, 2016

(86) PCT No.: PCT/EP2016/058086
§ 371 (c)(1),
(2) Date: Oct. 9, 2017

(87) PCT Pub. No.: WO2016/166140
PCT Pub. Date: Oct. 20, 2016

(65) Prior Publication Data
US 2018/0072868 A1 Mar. 15, 2018

(30) Foreign Application Priority Data

Apr. 16, 2015 (EP) ..................... 15163880

(51) Int. Cl.
| | | |
|---|---|---|
| *C08K 5/29* | (2006.01) | |
| *C07C 265/02* | (2006.01) | |
| *C07C 265/14* | (2006.01) | |
| *C08L 77/00* | (2006.01) | |

(52) U.S. Cl.
CPC .............. *C08K 5/29* (2013.01); *C07C 265/02* (2013.01); *C07C 265/14* (2013.01); *C08L 77/00* (2013.01); *C08J 2300/22* (2013.01)

(58) Field of Classification Search
CPC ....... C08K 5/29; C07C 265/02; C07C 265/14; C08L 77/00; C08J 2300/22
USPC ....................................................... 524/196
See application file for complete search history.

(56) References Cited

U.S. PATENT DOCUMENTS

| | | |
|---|---|---|
| 2,071,250 A | 2/1937 | Carothers |
| 2,071,251 A | 2/1937 | Carothers |
| 2,130,523 A | 9/1938 | Carothers |
| 2,130,948 A | 9/1938 | Carothers |
| 2,241,322 A | 5/1941 | Hanford |
| 2,312,966 A | 3/1943 | Hanford |
| 2,512,606 A | 6/1950 | Bolton et al. |
| 3,393,210 A | 7/1968 | Speck |
| 3,668,171 A | 6/1972 | Sims |
| 4,148,846 A | 4/1979 | Owens et al. |
| 4,360,617 A | 11/1982 | Muller et al. |
| 4,396,742 A | 8/1983 | Binsack et al. |
| 4,537,949 A | 8/1985 | Schmidt et al. |
| 4,540,772 A | 9/1985 | Pipper et al. |
| 4,600,752 A | 7/1986 | Meyer et al. |
| 4,771,109 A | 9/1988 | Eichenauer et al. |
| 4,873,289 A | 10/1989 | Lindner et al. |
| 4,882,381 A | 11/1989 | Wittmann et al. |
| 4,918,148 A * | 4/1990 | Meyer .................. C08G 18/603 524/196 |
| 5,010,135 A | 4/1991 | Eckel et al. |
| 5,272,236 A | 12/1993 | Lai et al. |
| 6,151,180 A | 11/2000 | Bang |
| 6,194,538 B1 | 2/2001 | Weiss et al. |
| 6,699,960 B1 | 3/2004 | Ohlbach et al. |
| 2003/0125429 A1 | 7/2003 | Joachimi et al. |
| 2005/0143548 A1 | 6/2005 | Loontjens et al. |
| 2006/0235191 A1 | 10/2006 | Deininger et al. |
| 2009/0012229 A1 | 1/2009 | Desbois et al. |

FOREIGN PATENT DOCUMENTS

| | | |
|---|---|---|
| DE | 2702661 A1 | 8/1977 |
| DE | 3725576 A1 | 2/1989 |
| DE | 3800603 A1 | 7/1989 |
| DE | 19916104 A1 | 10/1999 |
| DE | 10313681 A1 | 10/2004 |
| EP | 38094 A2 | 10/1981 |
| EP | 38582 A2 | 10/1981 |
| EP | 39524 A1 | 11/1981 |
| EP | 0050265 A1 | 4/1982 |

(Continued)

OTHER PUBLICATIONS

Extended European Search Report for EP Patent Application No. 15163880.6, dated Jul. 10, 2015 (7 pages).

(Continued)

*Primary Examiner* — Ling Siu Choi
*Assistant Examiner* — Ronald Grinsted
(74) *Attorney, Agent, or Firm* — Marshall, Gerstein & Borun LLP

(57) ABSTRACT

The invention relates to the use of thermoplastic molding compositions comprising D) from 30 to 99% by weight of a thermoplastic polyamide E) from 0.01 to 10% by weight of an organic isocyanate or diisocyanate, or a mixture of these F) from 0 to 60% by weight of other additional substances, where the sum of the percentages by weight of A) to C) is 100%, for the production of moldings of any type with improved haze (measured in accordance with ASTM D1003) and/or improved clarity (measured in accordance with ASTM D1003) and/or increased laser transparency (measured at a wavelength of 1064 nm by means of a thermoelectric power measurement).

7 Claims, No Drawings

(56) References Cited

FOREIGN PATENT DOCUMENTS

| | | |
|---|---|---|
| EP | 129195 A2 | 12/1984 |
| EP | 129196 A2 | 12/1984 |
| EP | 0208187 A2 | 1/1987 |
| EP | 0235690 A2 | 9/1987 |
| EP | 299444 A2 | 1/1989 |
| EP | 0319290 A2 | 6/1989 |
| EP | 922065 A2 | 6/1999 |
| EP | 1198491 A1 | 4/2002 |
| EP | 1994075 A2 | 11/2008 |
| JP | H08995 B2 | 1/1996 |
| WO | WO2012013988 * | 10/2012 |
| WO | WO-2013/139802 A1 | 9/2013 |

OTHER PUBLICATIONS

International Search Report for Patent Application No. PCT/EP2016/058086, dated Jun. 20, 2016.

* cited by examiner

POLYAMIDES WITH IMPROVED OPTICAL PROPERTIES

CROSS-REFERENCE TO RELATED APPLICATIONS

This application is the U.S. National Phase of PCT/EP2016/058086, filed Apr. 13, 2016, which claims the benefit of European Patent Application No. 15163880.6, filed Apr. 16, 2015.

The invention relates to the use of thermoplastic molding compositions comprising
A) from 30 to 99% by weight of a thermoplastic polyamide
B) from 0.01 to 10% by weight of an organic isocyanate or diisocyanate, or a mixture of these
C) from 0 to 60% by weight of other additional substances, where the sum of the percentages by weight of A) to C) is 100%,
for the production of moldings of any type type with improved haze (measured in accordance with ASTM D1003) and/or improved clarity (measured in accordance with ASTM D1003) and/or increased laser transparency (measured at a wavelength of 1064 nm by means of a thermoelectric power measurement).

The invention further relates to the use of transparent moldings and/or with reduced haze for the production of moldings of any type, in particular by means of laser transmission welding, and to the use of moldings of this type in various application sectors.

Polyamides are used in a great variety of applications, e.g. for motor vehicles, and electrical and electronic components, and as food-packaging material.

For certain application sectors, sheets, films, containers, headlamps, and similar components require greater transparency (in particular laser transparency) and reduced haze.

WO 2013/139802 discloses use of urea derivatives as additives for improving the optical properties of polyamides.

Use of diisocyanates or isocyanates in polyamides is disclosed inter alia in JP48000995 and U.S. Pat. No. 3,668,171. No mention is made of improvement of optical properties.

US2005/143548 describes a process for the production of a high-molecular-weight polyamide where a low-molecular-weight polyamide is mixed in the melt with a blocked diisocyanate. Use of blocked diisocyanates results in less discoloration of the polymer than use of unblocked diisocyanates. There is no mention in US 2005143548 of any favorable effect on the optical properties claimed in the present invention: haze, clarity and laser transparency.

It was therefore an object of the present invention to improve the optical properties of clarity (haze) and/or transparency (in particular laser transparency) in polyamides. Surprisingly, this object is achieved via addition of the isocyanates and/or diisocyanates of the invention to polyamides.

Accordingly, the use defined in the introduction has been found for the molding compositions. Preferred embodiments can be found in the dependent claims.

The molding compositions of the invention comprise, as component A), from 30 to 99% by weight, preferably from 30 to 98% by weight, and in particular from 30 to 90% by weight, of at least one polyamide.

The intrinsic viscosity of the polyamides of the molding compositions of the invention is generally from 90 to 350 ml/g, preferably from 110 to 240 ml/g auf, determined in 0.5% by weight solution in 96% by weight sulfuric acid at 25° C. in accordance with ISO 307.

Preference is given to semicrystalline or amorphous resins with a molecular weight (weight average) of at least 5 000, described by way of example in the following U.S. Pat. Nos. 2,071,250, 2,071,251, 2,130,523, 2,130,948, 2,241,322, 2,312,966, 2,512,606, and 3,393,210.

Examples of these are polyamides that derive from lactams having from 7 to 13 ring members, e.g. polycaprolactam, polycaprylolactam, and polylaurolactam, and also polyamides obtained via reaction of dicarboxylic acids with diamines.

Dicarboxylic acids which may be used are alkanedicarboxylic acids having 6 to 12, in particular 6 to 10, carbon atoms, and aromatic dicarboxylic acids. Acids that may be mentioned here, merely as examples, are adipic acid, azelaic acid, sebacic acid, dodecanedioic acid and terephthalic and/or isophthalic acid.

Particularly suitable diamines are alkanediamines having from 6 to 12, in particular from 6 to 8, carbon atoms, and also m-xylylenediamine (e.g. Ultramid® X17 from BASF SE, where the molar ratio of MXDA to adipic acid is 1:1), di(4-aminophenyl)methane, di(4-aminocyclohexyl)-methane, 2,2-di(4-aminophenyl)propane, 2,2-di(4-aminocyclohexyl)propane, and 1,5-diamino-2-methylpentane.

Preferred polyamides are polyhexamethyleneadipamide, polyhexamethylenesebacamide, and polycaprolactam, and also nylon-6/6,6 copolyamides, in particular having a proportion of from 5 to 95% by weight of caprolactam units (e.g. Ultramid® C31 from BASF SE).

Other suitable polyamides are obtainable from ω-aminoalkylnitriles, e.g. aminocapronitrile (PA 6) and adipodinitrile with hexamethylenediamine (PA 66) via what is known as direct polymerization in the presence of water, for example as described in DE-A 10313681, EP-A 1198491 and EP 922065.

Mention may also be made of polyamides obtainable, by way of example, via condensation of 1,4-diaminobutane with adipic acid at an elevated temperature (nylon-4,6). Preparation processes for polyamides of this structure are described by way of example in EP-A 38 094, EP-A 38 582, and EP-A 39 524.

Other suitable examples are polyamides obtainable via copolymerization of two or more of the abovementioned monomers, and mixtures of two or more polyamides in any desired mixing ratio. Particular preference is given to mixtures of nylon-6,6 with other polyamides, in particular nylon-6/6,6 copolyamides.

Other copolyamides which have proven particularly advantageous are semiaromatic copolyamides, such as PA 6/6T and PA 66/6T, where the triamine content of these is less than 0.5% by weight, preferably less than 0.3% by weight (see EP-A 299 444). Other polyamides resistant to high temperatures are known from EP-A 19 94 075 (PA 6T/6I/MXD6).

The processes described in EP-A 129 195 and 129 196 can be used to prepare the preferred semiaromatic copolyamides with low triamine content.

The following list, which is not comprehensive, comprises the polyamides A) mentioned and other polyamides A) for the purposes of the invention, and the monomers comprised:
AB Polymers:

| | |
|---|---|
| PA 4 | pyrrolidone |
| PA 6 | ε-caprolactam |
| PA 7 | ethanolactam |

| | |
|---|---|
| PA 8 | caprylolactam |
| PA 9 | 9-aminopelargonic acid |
| PA 11 | 11-aminoundecanoic acid |
| PA 12 | laurolactam |

AA/BB Polymers:

| | |
|---|---|
| PA 46 | tetramethylenediamine, adipic acid |
| PA 66 | hexamethylenediamine, adipic acid |
| PA 69 | hexamethylenediamine, azelaic acid |
| PA 610 | hexamethylenediamine, sebacic acid |
| PA 612 | hexamethylenediamine, decanedicarboxylic acid |
| PA 613 | hexamethylenediamine, undecanedicarboxylic acid |
| PA 1212 | 1,12-dodecanediamine, decanedicarboxylic acid |
| PA 1313 | 1,13-diaminotridecane, undecanedicarboxylic acid |
| PA 6T | hexamethylenediamine, terephthalic acid |
| PA 9T | 1,9-nonanediamine, terephthalic acid |
| PA MXD6 | m-xylylenediamine, adipic acid |
| PA 6I | hexamethylenediamine, isophthalic acid |
| PA 6-3-T | trimethylhexamethylenediamine, terephthalic acid |
| PA 6/6T | (see PA 6 and PA 6T) |
| PA 6/66 | (see PA 6 and PA 66) |
| PA 6/12 | (see PA 6 and PA 12) |
| PA 66/6/610 | (see PA 66, PA 6 and PA 610) |
| PA 6I/6T | (see PA 6I and PA 6T) |
| PA PACM 12 | diaminodicyclohexylmethane, laurolactam |
| PA 6I/6T/PACM | as PA 6I/6T + diaminodicyclohexylmethane |
| PA 12/MACMI | laurolactam, dimethyldiaminodicyclohexylmethane, isophthalic acid |
| PA 12/MACMT | laurolactam, dimethyldiaminodicyclohexylmethane, terephthalic acid |
| PA PDA-T | phenylenediamine, terephthalic acid |

The molding compositions that can be used in the invention comprise, as component B), from 0.01 to 10% by weight, preferably from 0.05 to 5% by weight, and in particular from 0.5 to 2% by weight, of an
organic isocyanate $R^1$—N═C═O or
diisocyanate O═C═N—$R^2$—N═C═O, or
a mixture of these,
where the moiety $R^1$ of component B) represents linear C1-C14-alkyl moieties, branched C3 to C12-alkyl moieties, unsubstituted or substituted C3 to C14-cycloalkyl moieties, or unsubstituted or substituted aromatic moieties having from 6 to 20 carbon atoms.

The expression linear alkyl moieties means unbranched alkyl chains having from 1 to 14, preferably from 1 to 10, carbon atoms. Examples that may be mentioned are methyl, ethyl, n-propyl, n-butyl, n-pentyl, n-hexyl, n-heptyl, n-octyl, n-nonyl and n-decyl.

The expression branched alkyl moieties means alkyl chains having branching which have from 3 to 12, preferably from 3 to 10, carbon atoms.

The following may be mentioned by way of example: isopropyl, 2-butyl, isobutyl, tert-butyl, 1-methylbutyl, 2-methylbutyl, 3-methylbutyl, 2,2-dimethylpropyl, 1-ethylpropyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-methylhexyl, 2-methylhexyl, 3-methylhexyl, 4-methylhexyl, 5-methylhexyl, 1-ethylpentyl, 2-ethylpentyl, 3-ethylpentyl, 1-methylheptyl, 2-methylheptyl, 3-methylheptyl, 4-methylheptyl, 5-methylheptyl, 1-propylpentyl, 1-ethylhexyl, 2-ethylhexyl, 3-ethylhexyl, 1-methyloctyl, 2-methylheptyl, 1-ethylhexyl, 2-ethylhexyl, 1,2-dimethylhexyl, 1-propylpentyl, and 2-propylpentyl.

Examples that may be mentioned as cycloalkyl moieties having from 3 to 14 carbon atoms, preferably from 3 to 10 carbon atoms, are cyclopropyl, cyclobutyl, cyclopentyl, cyclohexyl, cycloheptyl, cyclooctyl, cyclononyl and cyclodecyl.

The expression substituted cycloalkyl moieties means in particular cycloalkyl moieties which have a heteroatom, preferably N or O, within the ring, or can bear substituents such as one or more alkyl moieties having from 1 to 4 carbon atoms.

Examples of heterocyclic systems that may be mentioned are tetrahydrofuran and pyrrolidine.

The expression substituted aromatic moieties having from 6 to 20, preferably from 6 to 17, carbon atoms means aromatic ring systems such as phenyl, naphthyl, anthracenyl or phenanthryl.

These aromatic moieties can bear one or more substituents such as alkyl moieties (linear or branched, see definition above) having from 1 to 10, preferably from 1 to 4, carbon atoms, or halogen, preferably bromine or chlorine.

The aromatic moieties can moreover have bonding by way of alkylene bridges having from 1 to 4 carbon atoms to another aromatic moiety.

Preferred compounds that may be mentioned are cyclohexyl isocyanate, phenyl isocyanate, and tert-butyl isocyanate.

Preferred moieties $R^2$ are linear or branched C1 to C14-alkylene moieties, unsubstituted or substituted cycloalkylene moieties having from 3 to 17 carbon atoms, and substituted or unsubstituted aromatic moieties having from 6 to 20 carbon atoms.

Preferred alkylene moieties have from 1 to 10 carbon atoms. Examples that may be mentioned are methylene, ethylene, propylene, butylene, pentamethylene, hexamethylene, and heptamethylene.

Examples of branched alkylene chains are moieties defined above which can bear one or more alkyl moieties having from 1 to 4 carbon atoms.

Unsubstituted cycloalkylene moieties preferably have from 3 to 14 carbon atoms and comply with the above definition of cycloalkyl moieties, but a further H atom is replaced by a bond, thus forming a bivalent unit (or bivalent radical).

An example that may be mentioned is cyclohexylene or cyclopentylene.

Substituted cycloalkylene moieties can have heteroatoms such as N or O within the ring, or bear one or more alkyl moieties having from 1 to 4 carbon atoms. These moieties can moreover have bonding by way of alkylene bridges having from 1 to 4 carbon atoms to another cycloalkylene moiety, an example being

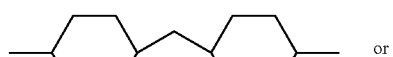

or

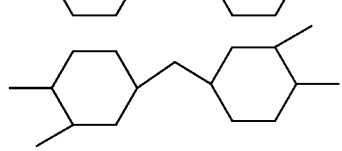

The expression substituted or unsubstituted aromatic moieties preferably having from 6 to 17 carbon atoms means abovementioned ring systems in which a further H atom has been replaced by a chemical bond, thus forming a bivalent unit (or bivalent radical).

Individual examples that may be mentioned are: aliphatic diisocyanates such as hexamethylene diisocyanate, cycloaliphatic diisocyanates such as isophorone diisocyanate, cyclohexane 1,4-diisocyanate, 1-methylcyclohexane 2,4- and 2,6-diisocyanate, and also the corresponding isomer mixtures, dicyclohexylmethane 4,4'-, 2,4'-, and 2,2'-diisocyanate, and also the corresponding isomer mixtures, and preferably aromatic diisocyanates such as tolylene 2,4-diisocyanate, mixtures of tolylene 2,4- and 2,6-diisocyanate, diphenylmethane 4,4'-, 2,4'-, and 2,2'-diisocyanate, mixtures of diphenylmethane 2,4'- and 4,4'-diisocyanate, 4,4'-diisocyanato-1,2-diphenylethane, and naphthylene 1,5-diisocyanate. It is preferable to use hexamethylene diisocyanate, isophorone diisocyanate, naphthylene 1,5-diisocyanate, diphenylmethane diisocyanate isomer mixtures with diphenylmethane 4,4'-diisocyanate content greater than 96% by weight, and in particular diphenylmethane 4,4'-diisocyanate.

Particular preference is given to:
cyclohexyl trans-1,4-diisocyanate (CAS 7517-76-2)
dicyclohexylmethane 4,4'-diisocyanate (CAS 5124-30-1)
methylenebis(phenyl 4,4'-diisocyanate) (CAS 101-68-8)
toluene 2,4-diisocyanate (CAS 584-84-9)
cyclohexyl isocyanate (CAS 3173-53-3)
phenylene 1,4-diisocyanate (CAS 104-49-4)
phenyl isocyanate (CAS 103-71-9), and
hexamethylene diisocyanate (CAS 822-06-0).

The molding compositions of the invention can comprise, as component C), from 0 to 60% by weight, preferably from 0 to 50% by weight, of other additional substances.

The molding compositions can comprise, as component C), quantities of from 0 to 40% by weight, preferably from 1 to 30% by weight, in particular from 2 to 20% by weight, of elastomeric polymers (also often termed impact modifiers, elastomers, or rubbers).

These are very generally copolymers preferably composed of at least two of the following monomers: ethylene, propylene, butadiene, isobutene, isoprene, chloroprene, vinyl acetate, styrene, acrylonitrile, and (meth)acrylates having from 1 to 18 carbon atoms in the alcohol component.

Polymers of this type are described by way of example in Houben-Weyl, Methoden der organischen Chemie, volume 14/1 (Georg-Thieme-Verlag, Stuttgart, 1961), pp 392 to 406, and in the monograph "Toughened Plastics" by C. B. Bucknall (Applied Science Publishers, London, 1977).

Some preferred types of these elastomers are described below.

Preferred types of these elastomers are those known as ethylene-propylene (EPM) and ethylene-propylene-diene (EPDM) rubbers.

EPM rubbers generally have practically no residual double bonds, whereas EPDM rubbers may have from 1 to 20 double bonds per 100 carbon atoms.

Examples which may be mentioned of diene monomers for EPDM rubbers are conjugated dienes, such as isoprene and butadiene, non-conjugated dienes having from 5 to 25 carbon atoms, such as 1,4-pentadiene, 1,4-hexadiene, 1,5-hexadiene, 2,5-dimethyl-1,5-hexadiene and 1,4-octadiene, cyclic dienes, such as cyclopentadiene, cyclohexadienes, cyclooctadienes and dicyclopentadiene, and also alkenylnorbornenes, such as 5-ethylidene-2-norbornene, 5-butylidene-2-norbornene, 2-methallyl-5-norbornene and 2-isopropenyl-5-norbornene, and tricyclodienes, such as 3-methyltricyclo[5.2.1.0$^{2,6}$]-3,8-decadiene, and mixtures of these. Preference is given to 1,5-hexadiene, 5-ethylidenenorbornene and dicyclopentadiene. The diene content of the EPDM rubbers is preferably from 0.5 to 50% by weight, in particular from 1 to 8% by weight, based on the total weight of the rubber.

EPM rubbers and EPDM rubbers may preferably also have been grafted with reactive carboxylic acids or with derivatives of these. Examples of these are acrylic acid, methacrylic acid and derivatives thereof, e.g. glycidyl (meth)acrylate, and also maleic anhydride.

Copolymers of ethylene with acrylic acid and/or methacrylic acid and/or with the esters of these acids are another group of preferred rubbers. The rubbers may also comprise dicarboxylic acids, such as maleic acid and fumaric acid, or derivatives of these acids, e.g. esters and anhydrides, and/or monomers comprising epoxy groups. These monomers comprising dicarboxylic acid derivatives or comprising epoxy groups are preferably incorporated into the rubber by adding to the monomer mixture monomers comprising dicarboxylic acid groups and/or epoxy groups and having the general formulae I or II or III or IV

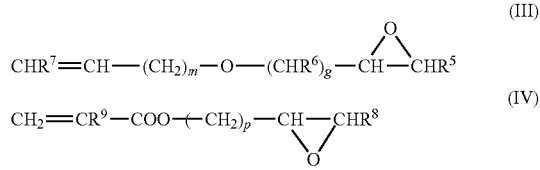

where $R^1$ to $R^9$ represent hydrogen or alkyl groups having from 1 to 6 carbon atoms, and m is a whole number from 0 to 20, g is a whole number from 0 to 10 and p is a whole number from 0 to 5. The radicals $R^1$ to $R^9$ are preferably hydrogen, where m is 0 or 1 and g is 1. The corresponding compounds are maleic acid, fumaric acid, maleic anhydride, allyl glycidyl ether and vinyl glycidyl ether.

Preferred compounds of the formulae I, II and IV are maleic acid, maleic anhydride and (meth)acrylates comprising epoxy groups, such as glycidyl acrylate and glycidyl methacrylate, and the esters with tertiary alcohols, such as tert-butyl acrylate. Although the latter have no free carboxy groups, their behavior approximates to that of the free acids and they are therefore termed monomers with latent carboxy groups. The copolymers are advantageously composed of from 50 to 98% by weight of ethylene, from 0.1 to 20% by weight of monomers comprising epoxy groups and/or methacrylic acid and/or monomers comprising anhydride groups, the remaining amount being (meth)acrylates.

Particular preference is given to copolymers composed of from 50 to 98% by weight, in particular from 55 to 95% by weight, of ethylene,
from 0.1 to 40% by weight, in particular from 0.3 to 20% by weight, of glycidyl acrylate and/or glycidyl methacrylate, (meth)acrylic acid and/or maleic anhydride, and
from 1 to 45% by weight, in particular from 5 to 40% by weight, of n-butyl acrylate and/or 2-ethylhexyl acrylate.

Other preferred (meth)acrylates are the methyl, ethyl, propyl, isobutyl and tert-butyl esters.

Comonomers which may be used alongside these are vinyl esters and vinyl ethers.

The ethylene copolymers described above may be prepared by processes known per se, preferably by random copolymerization at high pressure and elevated temperature. Appropriate processes are well-known.

Other preferred elastomers are emulsion polymers whose preparation is described, for example, in Blackley's monograph "Emulsion Polymerization". The emulsifiers and catalysts which can be used are known per se.

In principle it is possible to use homogeneously structured elastomers or else those with a shell structure. The shell-type structure is determined by the sequence of addition of the individual monomers. The morphology of the polymers is also affected by this sequence of addition.

Monomers which may be mentioned here merely as examples for the preparation of the rubber fraction of the elastomers are acrylates such as n-butyl acrylate and 2-ethylhexyl acrylate, corresponding methacrylates, butadiene and isoprene, and also mixtures of these. These monomers may be copolymerized with other monomers, such as styrene, acrylonitrile, vinyl ethers and with other acrylates or methacrylates, such as methyl methacrylate, methyl acrylate, ethyl acrylate or propyl acrylate.

The soft or rubber phase (with glass transition temperature below 0° C.) of the elastomers may be the core, the outer envelope or an intermediate shell (in the case of elastomers whose structure has more than two shells). Elastomers having more than one shell may also have more than one shell composed of a rubber phase.

If one or more hard components (with glass transition temperatures above 20° C.) are involved, besides the rubber phase, in the structure of the elastomer, these are generally prepared by polymerizing, as principal monomers, styrene, acrylonitrile, methacrylonitrile, α-methylstyrene, p-methylstyrene, or acrylates or methacrylates, such as methyl acrylate, ethyl acrylate or methyl methacrylate. Besides these, it is also possible to use relatively small proportions of other comonomers here.

It has proven advantageous in some cases to use emulsion polymers which have reactive groups at their surfaces. Examples of groups of this type are epoxy, carboxy, latent carboxy, amino and amide groups, and also functional groups which may be introduced by concomitant use of monomers of the general formula

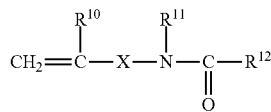

where the substituents can be defined as follows:
$R^{10}$ is hydrogen or a $C_1$-$C_4$-alkyl group,
$R^{11}$ is hydrogen, a $C_1$-$C_8$-alkyl group or an aryl group, in particular phenyl,
$R^{12}$ is hydrogen, a $C_1$-$C_{10}$-alkyl group, a $C_6$-$C_{12}$-aryl group, or —$OR^{13}$,
$R^{13}$ is a $C_1$-$C_8$-alkyl group or a $C_6$-$C_{12}$-aryl group, which can optionally have substitution by groups that comprise O or by groups that comprise N,
X is a chemical bond, a $C_1$-$C_{10}$-alkylene group, or a $C_6$-$C_{12}$-arylene group, or

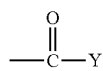

Y is O—Z or NH—Z, and
Z is a $C_1$-$C_{10}$-alkylene or $C_6$-$C_{12}$-arylene group.

The graft monomers described in EP-A 208 187 are also suitable for introducing reactive groups at the surface.

Other examples which may be mentioned are acrylamide, methacrylamide and substituted acrylates or methacrylates, such as (N-tert-butylamino)ethyl methacrylate, (N,N-dimethyl-amino)ethyl acrylate, (N,N-dimethylamino)methyl acrylate and (N,N-diethylamino)ethyl acrylate. The particles of the rubber phase may also have been crosslinked. Examples of crosslinking monomers are 1,3-butadiene, divinylbenzene, diallyl phthalate and dihydrodicyclopentadienyl acrylate, and also the compounds described in EP-A 50 265.

It is also possible to use the monomers known as graft-linking monomers, i.e. monomers having two or more polymerizable double bonds which react at different rates during the polymerization. Preference is given to the use of compounds of this type in which at least one reactive group polymerizes at about the same rate as the other monomers, while the other reactive group (or reactive groups), for example, polymerize(s) significantly more slowly. The different polymerization rates give rise to a certain proportion of unsaturated double bonds in the rubber. If another phase is then grafted onto a rubber of this type, at least some of the double bonds present in the rubber react with the graft monomers to form chemical bonds, i.e. the phase applied by grafting has at least some degree of chemical bonding to the graft base.

Examples of graft-linking monomers of this type are monomers comprising allyl groups, in particular allyl esters of ethylenically unsaturated carboxylic acids, for example allyl acrylate, allyl methacrylate, diallyl maleate, diallyl fumarate and diallyl itaconate, and the corresponding monoallyl compounds of these dicarboxylic acids. Besides these there is a wide variety of other suitable graft-linking monomers. For further details reference may be made here, for example, to U.S. Pat. No. 4,148,846.

The proportion of these crosslinking monomers in the impact-modifying polymer is generally up to 5% by weight, preferably not more than 3% by weight, based on the impact-modifying polymer.

Some preferred emulsion polymers are listed below. Mention may first be made here of graft polymers with a core and with at least one outer shell, and having the following structure:

| Type | Monomers for the core | Monomers for the envelope |
|---|---|---|
| I | 1,3-butadiene, isoprene, n-butyl acrylate, ethylhexyl acrylate, or a mixture of these | styrene, acrylonitrile, methyl methacrylate |
| II | as I, but with concomitant use of crosslinking agents | as I |
| III | as I or II | n-butyl acrylate, ethyl acrylate, methyl acrylate, 1,3-butadiene, isoprene, ethylhexyl acrylate |
| IV | as I or II | as I or III, but with concomitant use of monomers having reactive groups, as described herein |
| V | styrene, acrylonitrile, methyl methacrylate, or a mixture of these | first envelope composed of monomers as described under I and II for the core, second envelope as described under I or IV for the envelope |

Instead of graft polymers whose structure has more than one shell, it is also possible to use homogeneous, i.e. single-shell, elastomers composed of 1,3-butadiene, isoprene and n-butyl acrylate or of copolymers of these. These products, too, may be prepared by concomitant use of crosslinking monomers or of monomers having reactive groups.

Examples of preferred emulsion polymers are n-butyl acrylate-(meth)acrylic acid copolymers, n-butyl acrylate-glycidyl acrylate or n-butyl acrylate-glycidyl methacrylate copolymers, graft polymers with an inner core composed of n-butyl acrylate or based on butadiene and with an outer envelope composed of the abovementioned copolymers, and copolymers of ethylene with comonomers which supply reactive groups.

The elastomers described may also be prepared by other conventional processes, e.g. by suspension polymerization.

Preference is also given to silicone rubbers, as described in DE-A 37 25 576, EP-A 235 690, DE-A 38 00 603 and EP-A 319 290.

Particularly preferred rubbers C) are ethylene copolymers as described above which comprise functional monomers, where the functional monomers are those selected from the group of the carboxylic acid, carboxylic anhydride, carboxylic ester, carboxamide, carboximide, amino, hydroxy, epoxy, urethane, or oxazoline groups, or a mixture of these.

The content of the functional groups is from 0.1 to 20% by weight, preferably from 0.2 to 10% by weight, and in particular from 0.3 to 7% by weight, based on 100% by weight of C).

Particularly preferred monomers are those composed of an ethylenically unsaturated mono- or dicarboxylic acid or of a functional derivative of such an acid.

In principle, any of the primary, secondary, or tertiary $C_1$-$C_{18}$-alkyl (meth)acrylates is suitable, but preference is given to esters having from 1 to 12 carbon atoms, in particular having from 2 to 10 carbon atoms.

Examples here are methyl, ethyl, propyl, n-butyl, isobutyl and tert-butyl, 2-ethylhexyl, octyl and decyl acrylates, and the corresponding methacrylates. Among these, particular preference is given to n-butyl acrylate and 2-ethylhexyl acrylate.

The olefin polymers can also comprise, instead of the esters, or in addition to these, acid-functional and/or latently acid-functional monomers of ethylenically unsaturated mono- or dicarboxylic acids, or monomers having epoxy groups.

Other examples of monomers that may be mentioned are acrylic acid, methacrylic acid, tertiary alkyl esters of these acids, in particular tert-butyl acrylate, and dicarboxylic acids, such as maleic acid and fumaric acid, and derivatives of said acids, and also monoesters of these.

Latently acid-functional monomers are compounds which under the conditions of polymerization or during incorporation of the olefin polymers into the molding compositions, form free acid groups. Examples that may be mentioned here are anhydrides of dicarboxylic acids having up to 20 carbon atoms, in particular maleic anhydride, and tertiary $C_1$-$C_{12}$-alkyl esters of the above-mentioned acids, in particular tert-butyl acrylate and tert-butyl methacrylate.

The acid-functional or latently acid-functional monomers and the monomers comprising epoxy groups are preferably incorporated into the olefin polymers through addition of compounds of the general formulae I-IV to the monomer mixture.

The melt index of the ethylene copolymers is generally in the range from 1 to 80 g/10 min (measured at 190° C. with 2.16 kg load).

The molar mass of said ethylene-α-olefin copolymers is from 10 000 to 500 000 g/mol, preferably from 15 000 to 400 000 g/mol (Mn, determined by means of GPC in 1,2,4-trichlorobenzene with PS calibration).

One particular embodiment uses ethylene-α-olefin copolymers produced by means of "single site catalysts". Further details can be found in U.S. Pat. No. 5,272,236. In this case, the ethylene-α-olefin copolymers have a molecular weight distribution which is narrow for polyolefins: smaller than 4, and preferably smaller than 3.5.

Preferred commercially available products used are Exxelor® VA 1801, or 1803, Kraton® G 1901 FX, or Fusabond® N NM493 D, or Fusabond® A560 from Exxon, Kraton, and DuPont, and also Tafmer® MH 7010 from Mitsui.

It is also possible, of course, to use a mixture of the types of rubber listed above.

The molding compositions of the invention can comprise, as component C), up to 60% by weight, preferably up to 50% by weight, of other additional substances.

Fibrous or particulate fillers C) that may be mentioned are carbon fibers, glass fibers, glass beads, amorphous silica, calcium silicate, calcium metasilicate, magnesium carbonate, kaolin, chalk, powdered quartz, mica, barium sulfate, and feldspar, the amounts used of these being from 1 to 50% by weight, in particular from 5 to 40% by weight, preferably from 10 to 40% by weight.

Preferred fibrous fillers that may be mentioned are carbon fibers, aramid fibers, and potassium titanate fibers, particular preference being given to glass fibers in the form of E glass. These can be used as rovings or in the commercially available forms of chopped glass.

The fibrous fillers may have been surface-pretreated with a silane compound to improve compatibility with the thermoplastics.

Suitable silane compounds have the general formula

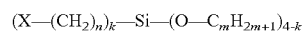

where the definitions of the substituents are as follows:

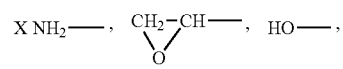

n is a whole number from 2 to 10, preferably 3 to 4,
m is a whole number from 1 to 5, preferably 1 to 2, and
k is a whole number from 1 to 3, preferably 1.

Preferred silane compounds are aminopropyltrimethoxysilane, aminobutyltrimethoxysilane, aminopropyltriethoxysilane and aminobutyltriethoxysilane, and also the corresponding silanes which comprise a glycidyl group as substituent X.

The amounts of the silane compounds generally used for surface-coating are from 0.01 to 2% by weight, preferably from 0.025 to 1.0% by weight and in particular from 0.05 to 0.5% by weight (based on C)).

Acicular mineral fillers are also suitable.

For the purposes of the invention, acicular mineral fillers are mineral fillers with strongly developed acicular character. An example is acicular wollastonite. The mineral preferably has an L/D (length to diameter) ratio of from 8:1 to 35:1, preferably from 8:1 to 11:1. The mineral filler may optionally have been pretreated with the abovementioned silane compounds, but the pretreatment is not essential.

Other fillers which may be mentioned are kaolin, calcined kaolin, wollastonite, talc and chalk, and also lamellar or acicular nanofillers, the amounts of these preferably being from 0.1 to 10%. Materials preferred for this purpose are boehmite, bentonite, montmorillonite, vermiculite, and hectorite. The lamellar nanofillers are organically modified by prior-art methods, to give them good compatibility with the organic binder. Addition of the lamellar or acicular nanofillers to the inventive nanocomposites gives a further increase in mechanical strength.

The molding compositions of the invention can comprise, as component C), from 0.05 to 3% by weight, preferably from 0.1 to 1.5% by weight, and in particular from 0.1 to 1% by weight, of a lubricant.

Preference is given to the salts of Al, of alkali metals, or of alkaline earth metals, or esters or amides of fatty acids having from 10 to 44 carbon atoms, preferably having from 12 to 44 carbon atoms.

The metal ions are preferably alkaline earth metal and Al, particular preference being given to Ca or Mg.

Preferred metal salts are Ca stearate and Ca montanate, and also Al stearate.

It is also possible to use a mixture of various salts, in any desired mixing ratio.

The carboxylic acids can be monobasic or dibasic. Examples which may be mentioned are pelargonic acid, palmitic acid, lauric acid, margaric acid, dodecanedioic acid, behenic acid, and particularly preferably stearic acid, capric acid, and also montanic acid (a mixture of fatty acids having from 30 to 40 carbon atoms).

The aliphatic alcohols can be monohydric to tetrahydric. Examples of alcohols are n-butanol, n-octanol, stearyl alcohol, ethylene glycol, propylene glycol, neopentyl glycol, pentaerythritol, preference being given to glycerol and pentaerythritol.

The aliphatic amines can be mono- to tribasic. Examples of these are stearylamine, ethylenediamine, propylenediamine, hexamethylenediamine, di(6-aminohexyl)amine, particular preference being given to ethylenediamine and hexamethylenediamine. Preferred esters or amides are correspondingly glycerol distearate, glycerol tristearate, ethylenediamine distearate, glycerol monopalmitate, glycerol trilaurate, glycerol monobehenate, and pentaerythritol tetrastearate.

It is also possible to use a mixture of various esters or amides, or of esters with amides in combination, in any desired mixing ratio.

Suitable sterically hindered phenols C) are in principle any of the compounds having phenolic structure which have at least one bulky group on the phenolic ring.

It is preferable to use by way of example compounds of the formula

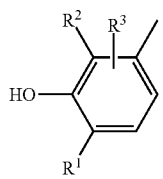

where:

$R^1$ and $R^2$ are an alkyl group, a substituted alkyl group, or a substituted triazole group, and where the radicals $R^1$ and $R^2$ may be identical or different, and $R^3$ is an alkyl group, a substituted alkyl group, an alkoxy group, or a substituted amino group.

Antioxidants of the abovementioned type are described by way of example in DE-A 27 02 661 (U.S. Pat. No. 4,360, 617).

Another group of preferred sterically hindered phenols is provided by those derived from substituted benzenecarboxylic acids, in particular from substituted benzenepropionic acids.

Particularly preferred compounds from this class are compounds of the formula

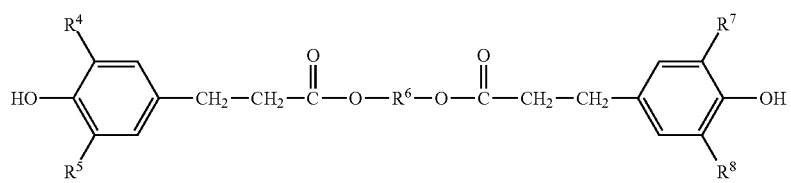

where $R^4$, $R^5$, $R^7$, and $R^8$, independently of one another, are $C_1$-$C_8$-alkyl groups which themselves may have substitution (at least one of these being a bulky group), and $R^6$ is a divalent aliphatic radical which has from 1 to 10 carbon atoms and whose main chain may also have C—O bonds.

Preferred compounds corresponding to this formula are

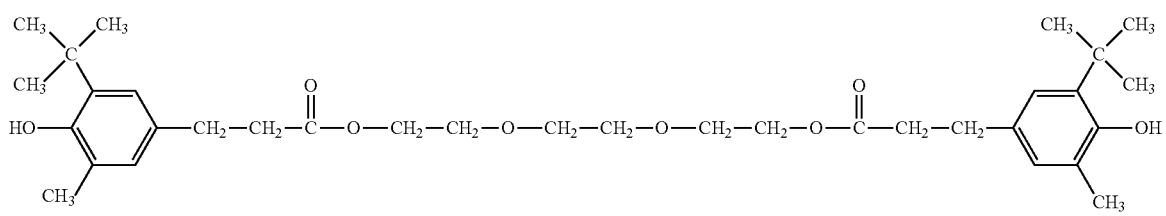

(Irganox® 245 from BASF SE)

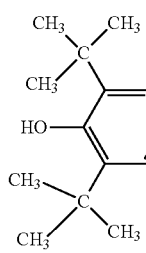 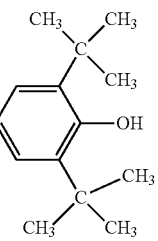

(Irganox® 259 from BASF SE)

All of the following should be mentioned as examples of sterically hindered phenols:

2,2'-methylenebis(4-methyl-6-tert-butylphenol), 1,6-hexanediol bis[3-(3,5-di-tert-butyl-4-hydroxyphenyl)propionate], pentaerythrityl tetrakis[3-(3,5-di-tert-butyl-4-hydroxyphenyl)-propionate], distearyl 3,5-di-tert-butyl-4-hydroxybenzylphosphonate, 2,6,7-trioxa-1-phosphabicyclo[2.2.2]oct-4-ylmethyl 3,5-di-tert-butyl-4-hydroxyhydrocinnamate, 3,5-di-tert-butyl-4-hydroxyphenyl-3,5-distearylthiotriazylamine, 2-(2'-hydroxy-3'-hydroxy-3',5'-di-tert-butylphenyl)-5-chlorobenzotriazole, 2,6-di-tert-butyl-4-hydroxymethylphenol, 1,3,5-trimethyl-2,4,6-tris(3,5-di-tert-butyl-4-hydroxybenzyl)benzene, 4,4'-methylenebis(2,6-di-tert-butylphenol), 3,5-di-tert-butyl-4-hydroxybenzyldimethylamine.

Compounds which have proven particularly effective and which are therefore used with preference are 2,2'-methylenebis(4-methyl-6-tert-butylphenol), 1,6-hexanediol bis(3,5-di-tert-butyl-4-hydroxyphenyl)propionate (Irganox® 259), pentaerythrityl tetrakis[3-(3,5-di-tert-butyl-4-hydroxyphenyl)propionate], and also N,N'-hexamethylenebis-3,5-di-tert-butyl-4-hydroxyhydrocinnamide (Irganox® 1098), and the product Irganox® 245 described above from BASF SE, which has particularly good suitability.

The quantity of the antioxidants C) which can be used, individually or as mixtures, is from 0.05 up to 3% by weight, preferably from 0.1 to 1.5% by weight, in particular from 0.1 to 1% by weight, based on the total weight of the molding compositions A) to C).

In some instances, sterically hindered phenols having not more than one sterically hindered group in ortho-position with respect to the phenolic hydroxy group have proven particularly advantageous; in particular when assessing colorfastness on storage in diffuse light over prolonged periods.

The molding compositions of the invention can comprise, as component C), from 0.05 to 5% by weight, preferably from 0.1 to 2% by weight, and in particular from 0.25 to 1.5% by weight, of a nigrosin.

Nigrosins are generally a group of black or gray phenazine dyes (azine dyes) related to the indulines and taking various forms (water-soluble, liposoluble, spirit-soluble), used in wool dyeing and wool printing, in black dyeing of silks, and in the coloring of leather, of shoe creams, of varnishes, of plastics, of stoving lacquers, of inks, and the like, and also as microscopy dyes.

Nigrosins are obtained industrially via heating of nitrobenzene, aniline, and aniline hydrochloride with metallic iron and FeCl₃ (the name being derived from the Latin niger=black).

Component C) can be used in the form of free base or else in the form of salt (e.g. hydrochloride).

Further details concerning nigrosins can be found by way of example in the electronic encyclopedia Römpp Online, Version 2.8, Thieme-Verlag Stuttgart, 2006, keyword "Nigrosin".

The molding compositions of the invention can comprise, as component C), from 0 to 20% by weight, preferably from 1 to 15% by weight, and in particular from 5 to 15% by weight, of red phosphorus or/and of a nitrogen-containing flame retardant, preferably a melamine compound.

Suitable compounds (often also termed salts or adducts) are melamine sulfate, melamine, melamine borate, melamine oxalate, melamine phosphate prim., melamine phosphate sec., and melamine pyrophosphate sec., melamine neopentyl glycol borate, and also polymeric melamine phosphate (CAS No. 56386-64-2 and 218768-84-4).

The thermoplastic molding compositions of the invention can comprise, as component C), conventional processing aids such as stabilizers, oxidation retarders, agents to counteract decomposition by heat and decomposition by ultraviolet light, lubricants and mold-release agents, colorants such as dyes and pigments, nucleating agents, plasticizers, etc.

Examples of oxidation retarders and heat stabilizers are sterically hindered phenols and/or phosphites and amines (e.g. TAD), hydroquinones, aromatic secondary amines, such as diphenylamines, various substituted members of these groups, and mixtures of these, in concentrations of up to 1% by weight, based on the weight of the thermoplastic molding compositions.

UV stabilizers that may be mentioned, the amounts of which used are generally up to 2% by weight, based on the molding composition, are various substituted resorcinols, salicylates, benzotriazoles, and benzophenones.

Materials that can be added as colorants are inorganic pigments, such as titanium dioxide, ultramarine blue, iron oxide, and carbon black, and also organic pigments, such as phthalocyanines, quinacridones, perylenes, and also dyes, such as anthraquinones.

Materials that can be used as nucleating agents are sodium phenylphosphinate, aluminum oxide, silicon dioxide, and also preferably talc powder.

The thermoplastic molding compositions of the invention can be produced by processes known per se, by mixing the starting components in conventional mixing apparatus, such as screw-based extruders, Brabender mixers, or Banbury mixers, and then extruding the same. The extrudate can be cooled and pelletized. It is also possible to premix individual components and then to add the remaining starting materials individually and/or likewise mixed. The mixing temperatures are generally from 230 to 320° C.

According to another preferred mode of operation, components B), and also optionally C), can be mixed with a prepolymer, compounded, and pelletized. The resultant pellets are then solid-phase-condensed continuously or batchwise under inert gas at a temperature below the melting point of component A) until the desired viscosity has been reached.

The molding compositions that can be used in the invention are suitable for the production of moldings of any type which have improved (laser) transparency and/or reduced haze. These molding compositions have at least one of the following advantages:

the haze value is at least 5% lower than that of a reference polymer composition without component B), measured in accordance with ASTM D1003 (from a test sample of thickness 1.3 mm);

the clarity value is at least 5% higher than that of a reference polymer composition without component B), measured in accordance with ASTM D1003 (from a test sample of thickness 1.3 mm);

laser transparency is at least 1% higher than that of a reference polymer composition without component B), measured at 1064 nm (from a test sample of thickness 1.3 mm).

The term "haze" used here is defined as the percentage of transmitted light which deviates on average by more than 2.5° from the incident light as a result of passage through a sample (sheet). Haze is determined in accordance with ASTM D1003. The haze of the molding compositions that can be used in the invention is at least 5% lower, preferably 10% lower, particularly preferably 15% lower, and in particular 20% lower, than that of a reference polymer composition without component B), measured from a sample (sheet) of thickness 1.3 mm.

The term "clarity" used here is defined as the percentage of transmitted light which deviates by less than 2.5° from the incident light as a result of passage through a sample (sheet). Clarity is determined in accordance with ASTM D1003. The clarity of the molding compositions that can be used in the invention is at least 5% higher, preferably 10% higher, particularly preferably 15% higher, and in particular 20% higher, than that of a reference polymer composition without component B), measured from a sample (sheet) of thickness 1.3 mm.

The laser transparency of the molding compositions that can be used in the invention is at least 1% higher, preferably 3% higher, particularly preferably 5% higher, and in particular 10% higher, than that of a reference polymer composition without component B), measured from a test sample (sheet) of thickness 1.3 mm.

A thermoelectric power measurement was used to determine laser transmittance at wavelength 1064 nm. The measurement geometry was set up as follows:

A beam divider (SQ2 nonpolarizing beam divider from Laseroptik GmbH) was used to divide a reference beam of power 1 Watt at an angle of 90° from a laser beam (diode-pumped Nd-YAG laser of wavelength 1064 nm, FOBA DP50) with total power of 2 Watts. The reference beam impacted the reference sensor. That portion of the original beam that passed through the beam divider provided the measurement beam likewise with power of 1 Watt. This beam was focused to focal diameter 0.18 μm via a mode diaphragm (5.0) behind the beam divider. The laser transparency (LT) measurement sensor was positioned 80 mm below the focus. The test sheet was positioned 2 mm above the LT measurement sensor. The total measurement time was 30 s, the measurement result being determined within the final 5 s. The signals from reference sensor and measurement sensor were captured simultaneously. The start of the measurement was simultaneous with the insertion of the sample.

Transmission, and with this laser transparency, was obtained from the following formula: LT=(signal(measurement sensor)/signal(reference sensor))×100%. This method of measurement excluded variations of the laser system and subjective reading errors. These laser-transparent moldings are used in the invention for the production of moldings by means of laser transmission welding processes.

Laser-absorbent molding used can generally be moldings made of any laser-absorbent materials. These can by way of example be composite materials, thermosets, or preferred moldings made of suitable thermoplastic molding compositions. Suitable thermoplastic molding compositions are molding compositions which have adequate laser absorption in the wavelength range used. Suitable thermoplastic molding compositions can by way of example preferably be thermoplastics which are laser-absorbent by virtue of addition of inorganic pigments such as carbon black and/or by virtue of addition of organic pigments or other additives. Suitable organic pigments for achieving laser absorption are by way of example preferably IR-absorbent organic compounds as described by way of example in DE 199 16 104 A1.

The invention further provides moldings and/or molding combinations to which moldings of the invention have been bonded by laser transmission welding.

Moldings of the invention have excellent suitability for durable and stable attachment to laser-absorbent moldings by the laser transmission welding process. They are therefore in particular suitable for materials for covers, housings, add-on parts, and sensors by way of example for the following applications: motor vehicle, electronics, telecommunications, information technology, computer, household, sports, medical, and entertainment.

EXAMPLES

The following components were used:

Component A/1

Nylon-6 with intrinsic viscosity IV 150 ml/g, measured on a 0.5% by weight solution in 96% by weight sulfuric acid at 25° C. in accordance with ISO 307 (the material used being Ultramid® B27 from BASF SE).

Component A/2

PA 66 with IV 150 ml/g (Ultramid® A27 from BASF SE)

Materials:

B1 cyclohexyl trans-1,4-diisocyanate (CAS 7517-76-2)

B2 hexamethylene diisocyanate (CAS 822-06-0)

B3 dicyclohexylmethane 4,4'-diisocyanate (CAS 5124-30-1)

B4 methylenebis(phenyl 4,4'-diisocyanate) (CAS 101-68-8)

B5 toluene 2,4-diisocyanate (CAS 584-84-9)

B6 cyclohexyl isocyanate (CAS 3173-53-3)

B7 phenylene 1,4-diisocyanate (CAS 104-49-4)

B8 phenyl isocyanate (CAS 103-71-9)

B9 isophorone diisocyanate (CAS 4098-71-9)

Structural Formulae:

B1 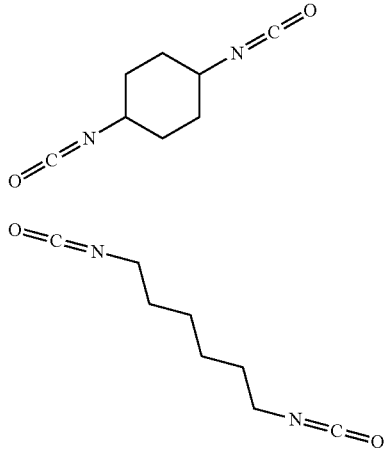

B2 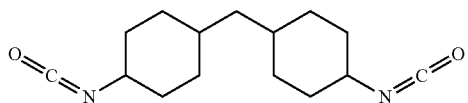

B3 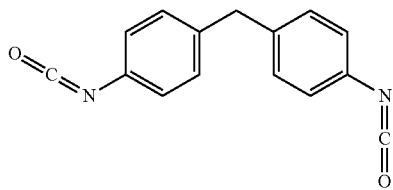

B4 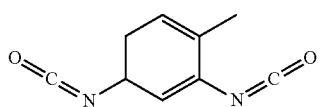

B5 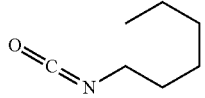

B6 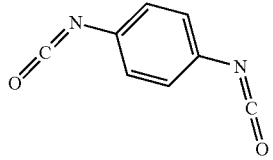

B7 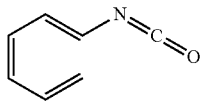

B8 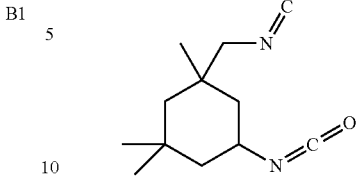

-continued

B9 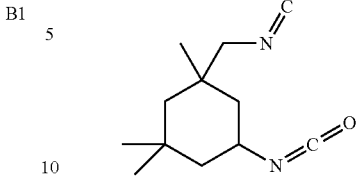

Processing:

Compounding—DSM:

The polyamide pellets and the respective isocyanates (1% by weight) were weighed into a glass flask and then incorporated by compounding under nitrogen in a conical twin-screw extruder (DSM Xplore, 15 cc). The polyamide without additional materials was processed in the same manner to obtain the reference sample. The following parameters were used:

Residence time: 3 min.

Barrel temperature: 260° C.

Melt temperature: from 240° C. to 245° C.

Rotation rate: 200 rpm

Injection Molding—DSM:

The compounded polymers were injection-molded in a 10 cc DSM Micro-Injection molding apparatus. For this, the molten compounded material was charged under nitrogen directly to the cylinder of the injection-molding machine. The melt was then injected into a polished rectangular mold measuring 30 mm×30 mm×1.27 mm. The following parameters were used:

Mold: Plaque, polished; 30 mm×30 mm×1.27 mm

Mold temperature: 70° C.

Cylinder temperature: 260° C.

Injection pressure: from 10 to 12 bar

Measurement Methods:

Polymer Crystallization Temperature

The crystallization behavior of the polymer mixtures is determined by means of differential scanning calorimetry (DSC) in a manner known per se (ISO 11357-2:2013). The determination is carried out under nitrogen in open aluminum crucibles at a heating rate and cooling rate of 20 K/min. After the first heating procedure the sample is retained in the melt for 5 min in order to delete the thermal history of the polymer. The DSC measurement is advantageously repeated once or twice on the same sample, in order to ensure that the respective polyamide has a defined thermal history. The crystallization temperature Tk was determined in accordance with DIN EN ISO 11357-3. The crystallization temperature Tk is the exothermic peak minimum of the DSC curve during the first cooling procedure at 20 K/min after a defined thermal history.

Optical Characterization (Haze, Clarity):

Haze, clarity, and transmission were measured with a haze gard plus tester (BYK-G, Gardner®, illumination CIE-E) at room temperature. The measurement was made in accordance with ASTM D1003. The time elapsed after the injection-molding process for measurement of the haze and clarity values was from 24 to 48 h.

TABLE 1

Composition of the compounded materials

| Ex. No. | A/1 (% by wt.) | A/2 (%) | B1 (%) | B2 (%) | B3 (%) | B4 (%) | B5 (%) | B6 (%) | B7 (%) | B8 (%) | B9 (%) |
|---|---|---|---|---|---|---|---|---|---|---|---|
| 1 comp. | 100 | 0 | 0 | 0 | 0 | 0 | 0 | 0 | 0 | 0 | 0 |
| 2 | 99 | 0 | 1 | 0 | 0 | 0 | 0 | 0 | 0 | 0 | 0 |
| 3 | 99 | 0 | 0 | 1 | 0 | 0 | 0 | 0 | 0 | 0 | 0 |
| 4 | 99 | 0 | 0 | 0 | 0 | 0 | 0 | 0 | 0 | 0 | 0 |
| 5 | 99 | 0 | 0 | 0 | 1 | 0 | 0 | 0 | 0 | 0 | 0 |
| 6 | 99 | 0 | 0 | 0 | 0 | 1 | 0 | 0 | 0 | 0 | 0 |
| 7 | 99 | 0 | 0 | 0 | 0 | 0 | 1 | 0 | 0 | 0 | 0 |
| 8 | 99 | 0 | 0 | 0 | 0 | 0 | 0 | 1 | 0 | 0 | 0 |
| 9 | 99 | 0 | 0 | 0 | 0 | 0 | 0 | 0 | 1 | 0 | 0 |
| 10 | 99 | 0 | 0 | 0 | 0 | 0 | 0 | 0 | 0 | 1 | 0 |
| 11 | 99 | 0 | 0 | 0 | 0 | 0 | 0 | 0 | 0 | 0 | 1 |
| 12 comp. | 0 | 100 | 0 | 0 | 0 | 0 | 0 | 0 | 0 | 0 | 0 |
| 13 | 0 | 99 | 1 | 0 | 0 | 0 | 0 | 0 | 0 | 0 | 0 |

TABLE 2

| Composition | Haze [%] | Clarity [%] |
|---|---|---|
| 1 comp. | 99.8 | 63.6 |
| 2 | 25.5 | 97.4 |
| 3 | 72.7 | 59.5 |
| 4 | 95.4 | 55.9 |
| 5 | 97.5 | 30.3 |
| 6 | 96.1 | 82.2 |
| 7 | 80.1 | 41.8 |
| 8 | 92.5 | 9.1 |
| 9 | 86.7 | 88.2 |
| 10 | 91.6 | 24.1 |
| 11 | 97.2 | 28.7 |
| 12 comp. | 99.6 | 5.5 |
| 13 | 63.6 | 96.1 |

The invention claimed is:

1. A method of producing a molding comprising a thermoplastic molding composition comprising admixing
   A) from 30 to 99% by weight of a thermoplastic polyamide selected from the group consisting of PA 6 and PA 66,
   B) from 0.01 to 10% by weight of cyclohexyl trans-1,4-diisocyanate and phenylene 1,4-diisocyanate, and
   C) from 0 to 60% by weight of other additional substances,
   where the sum of the percentages by weight of A) to C) is 100% and the thermoplastic molding composition is free of polyoxymethylene,
   wherein the molding has improved haze, measured in accordance with ASTM D1003, and/or improved clarity, measured in accordance with ASTM D1003, and/or increased laser transparency, measured at a wavelength of 1064 nm by means of a thermoelectric power measurement,
   wherein the haze value of the molding, measured in accordance with ASTM D1003, is at least 5% lower than that of a reference polymer composition without component B), measured from a test sample of thickness 1.3 mm,
   wherein the clarity value of the molding, measured in accordance with ASTM D1003, is at least 5% higher than that of a reference polymer composition without component B), measured from a test sample of thickness 1.3 mm, and
   wherein the laser transparency of the molding, measured at a wavelength of 1064 nm by means of a thermoelectric power measurement, is at least 1% higher than that of a reference polymer composition without component B), measured from a test sample of thickness 1.3 mm.

2. The method according to claim 1, where the thermoplastic molding composition comprises
   A) from 30 to 99% by weight,
   B) from 0.01 to 5% by weight, and
   C) from 0 to 50% by weight.

3. The method according to claim 1, further comprising an organic isocyanate compound of formula R1–N=C=O, where the moiety R1 represents linear C1-c14-alkyl moieties, branched C3 to C12-alkyl moieties, unsubstituted or substituted C3 to C14-cyclo-alkyl moieties, or unsubstituted or substituted aromatic moieties having from 6 to 20 carbon atoms.

4. The method according to claim 3 wherein the further organic isocyanate compound is selected from the group consisting of:
   cyclohexyl isocyanate and
   phenyl isocyanate.

5. The method according to claim 1 further comprising extruding the thermoplastic molding composition.

6. The method according to claim 1 further comprising pelletizing the thermoplastic molding composition.

7. The method according to claim 1 wherein the thermoplastic molding composition comprises 0.5 to 2% by weight of the organic diisocyanate B).

* * * * *